(12) United States Patent
Uhr

(10) Patent No.: US 10,035,308 B2
(45) Date of Patent: Jul. 31, 2018

(54) BONE REGENERATION MATERIAL

(71) Applicant: NOBEL BIOCARE SERVICES AG, Kloten (CH)

(72) Inventor: Günter Uhr, Zurich (CH)

(73) Assignee: Nobel Biocare Services AG, Kloten (CH)

(*) Notice: Subject to any disclaimer, the term of this patent is extended or adjusted under 35 U.S.C. 154(b) by 259 days.

(21) Appl. No.: 14/419,075

(22) PCT Filed: Aug. 5, 2013

(86) PCT No.: PCT/EP2013/002335
§ 371 (c)(1),
(2) Date: Feb. 2, 2015

(87) PCT Pub. No.: WO2014/019712
PCT Pub. Date: Feb. 6, 2014

(65) Prior Publication Data
US 2015/0190969 A1  Jul. 9, 2015

(30) Foreign Application Priority Data
Aug. 3, 2012 (GB) .................................. 1213845.9

(51) Int. Cl.
*A61F 2/00* (2006.01)
*B29C 67/00* (2017.01)
(Continued)

(52) U.S. Cl.
CPC ............ *B29C 67/0088* (2013.01); *A61F 2/28* (2013.01); *A61F 2/2803* (2013.01);
(Continued)

(58) Field of Classification Search
CPC ........ A61B 17/3472; A61B 2017/8838; A61B 5/02141
See application file for complete search history.

(56) References Cited

U.S. PATENT DOCUMENTS

| 5,248,506 A | 9/1993 | Holme et al. |
| 6,296,667 B1 * | 10/2001 | Johnson ................. A61F 2/28 623/23.61 |

(Continued)

FOREIGN PATENT DOCUMENTS

| CN | 101 057 979 A | 10/2007 |
| CN | 101285841 A | 10/2008 |

(Continued)

OTHER PUBLICATIONS

International Search Report for Application No. PCT/EP2013/001985 dated Sep. 3, 2013 in 3 pages.
(Continued)

*Primary Examiner* — Ann Schillinger
(74) *Attorney, Agent, or Firm* — Knobbe, Martens, Olson & Bear LLP

(57) ABSTRACT

A method of manufacturing a bone substitute structure for reconstruction of bone material in a patient. The method comprises the steps of providing data reflecting a cavity in a bone of a patient, defining and modelling a three dimensional structure corresponding to the cavity in the bone; and providing an individualized bone substitute structure, corresponding to the defined and modeled three dimensional structure, by combining calcium phosphate cement, growth factors and the patient's own un-coagulated blood.

10 Claims, 1 Drawing Sheet

(51) Int. Cl.
  *A61F 2/28*    (2006.01)
  *A61F 2/30*    (2006.01)
  *A61L 27/36*   (2006.01)
  *A61L 27/42*   (2006.01)
  *A61L 27/54*   (2006.01)
  *G05B 15/02*   (2006.01)
  *G06F 17/50*   (2006.01)
  *B33Y 50/00*   (2015.01)
  *B33Y 10/00*   (2015.01)
  *B33Y 30/00*   (2015.01)
  *B33Y 50/02*   (2015.01)
  *B33Y 70/00*   (2015.01)
  *B33Y 80/00*   (2015.01)

(52) U.S. Cl.
  CPC ...... *A61F 2/30942* (2013.01); *A61L 27/3616* (2013.01); *A61L 27/425* (2013.01); *A61L 27/54* (2013.01); *G05B 15/02* (2013.01); *G06F 17/50* (2013.01); *A61F 2002/2817* (2013.01); *A61F 2002/2835* (2013.01); *A61F 2002/30948* (2013.01); *A61F 2002/30952* (2013.01); *B33Y 10/00* (2014.12); *B33Y 30/00* (2014.12); *B33Y 50/00* (2014.12); *B33Y 50/02* (2014.12); *B33Y 70/00* (2014.12); *B33Y 80/00* (2014.12)

(56) References Cited

U.S. PATENT DOCUMENTS

| | | | |
|---|---|---|---|
| 6,905,516 | B1 * | 6/2005 | Lemaitre ............... A61F 2/28 623/23.56 |
| 2003/0175248 | A1 | 9/2003 | Uhr |
| 2003/0180274 | A1 | 9/2003 | Uhr |
| 2005/0074433 | A1 | 4/2005 | Stoll |
| 2006/0225620 | A1 | 10/2006 | Murphy et al. |
| 2007/0020607 | A1 | 1/2007 | Meryman et al. |
| 2007/0283849 | A1 | 12/2007 | Edidin et al. |
| 2008/0033572 | A1 | 2/2008 | D'Antonio et al. |
| 2011/0112654 | A1 | 5/2011 | Faldt |

FOREIGN PATENT DOCUMENTS

| | | |
|---|---|---|
| CN | 101 672 853 A | 3/2010 |
| CN | 102 188 362 A | 9/2011 |
| CN | 102 422 835 A | 4/2012 |
| EP | 2055268 A1 * | 8/2007 |
| EP | 2 055 268 A1 | 5/2009 |
| JP | 2004-505747 | 2/2004 |
| WO | WO 92/08348 A1 | 5/1992 |
| WO | WO 00/44305 A1 | 8/2000 |
| WO | WO 01/66044 A2 | 9/2001 |
| WO | WO 01/85040 A1 | 11/2001 |
| WO | WO 01/94349 A1 | 12/2001 |
| WO | WO 02/15950 A1 | 2/2002 |
| WO | WO 02/32827 A1 | 4/2002 |
| WO | WO 2004/112631 A1 | 12/2004 |
| WO | WO 2006/130455 A2 | 12/2006 |
| WO | WO 2008/022478 | 2/2008 |
| WO | WO 2010/148229 A1 | 12/2010 |
| WO | WO 2012/070052 A1 | 5/2012 |
| WO | WO 2014/012630 A1 | 1/2014 |
| WO | WO 2014/012631 A1 | 1/2014 |

OTHER PUBLICATIONS

International Search Report for Application No. PCT/EP2013/002335 dated Nov. 25, 2013 in 4 pages (ISR for the PCT application of this national phase application).

International Search Report for Application No. PCT/EP2013/001981 dated Sep. 27, 2013 in 4 pages.

De Jonge et al., Organic-inorganic surface modifications for titanium implant surfaces. Pharmaceutical Res vol. 25, No. 10, 2357-2369 (Oct. 2008).

Eriksson C. et al., Implantation of hydrophilic and hydrophobic titanium discs in rat tibia :cellular reactions on the surfaces during the first 3 weeks in bone. Biomaterials 25, 4759-4766 (2004).

Kennedy S.B. et al., Combinatorial screen of the effect of surface energy on fibronectin-mediated osteoblast adhesion, spreading and proliferation. Biomaterials 27, 3817-3824 (2006).

* cited by examiner

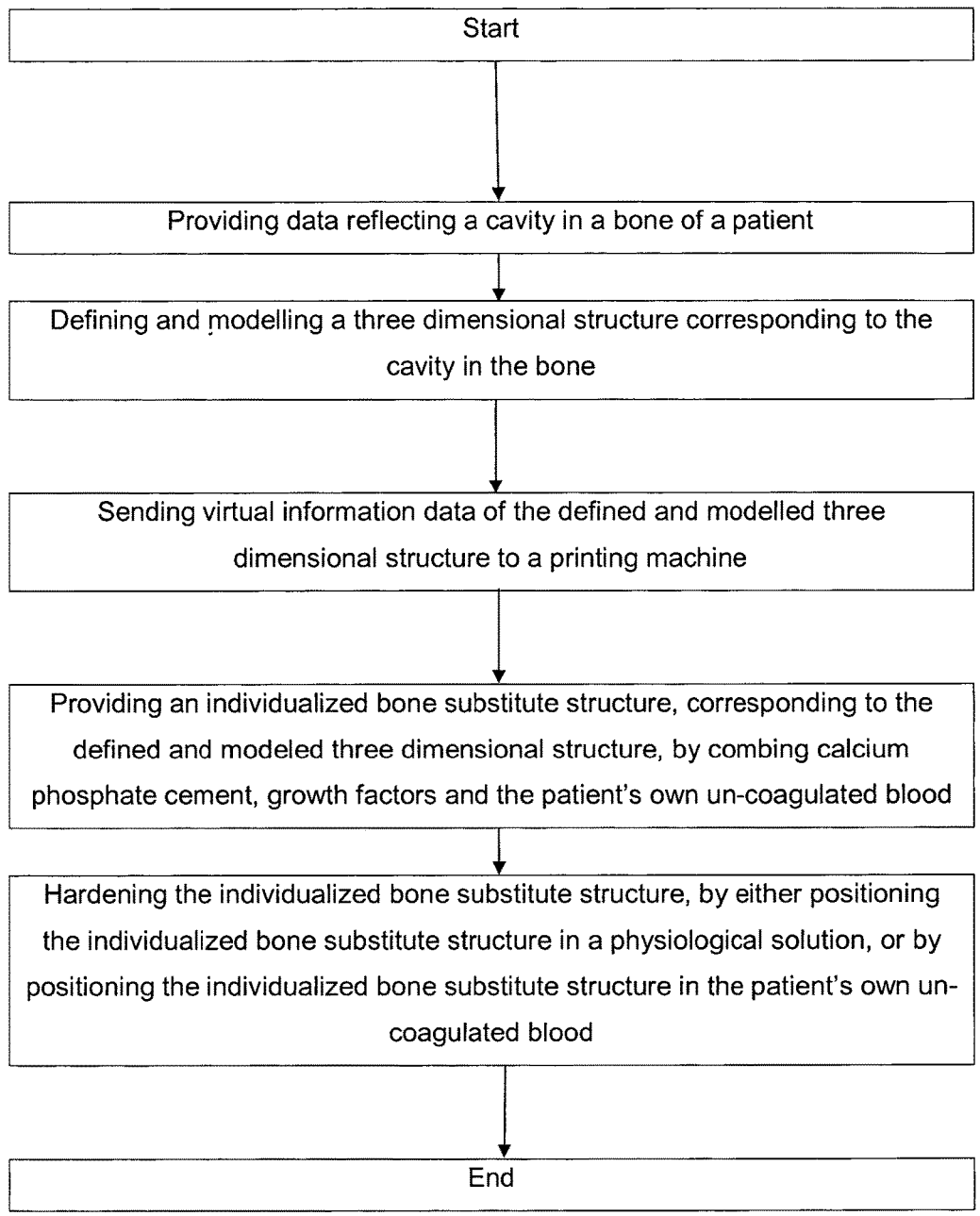

BONE REGENERATION MATERIAL

CROSS-REFERENCE TO RELATED APPLICATIONS

This application is a national stage application under 35 U.S.C. § 371 of International Application No. PCT/EP2013/002335, filed on Aug. 5, 2013, which published in English as WO 2014/019712 A1 on Feb. 6, 2014 and which claims priority benefit of GB Patent Application No. 1213845.9 filed on Aug. 3, 2012.

TECHNICAL FIELD

The present invention relates to the field of reconstruction of bone material, and more particularly, to reconstruction of bone cavities within the field of restorative and esthetic dental solutions.

BACKGROUND

Reconstruction of bone cavities or large bone defects is a challenge in reconstructive surgery. Today, such bone cavities or defects are usually treated with autologous (or autogenous) bone transplants, where the bone is obtained from the same individual receiving the autologous bone transplant. This is also known as an autologous grafting, meaning the donor of the bone and the recipient of the bone are the same, and grafting is a surgical procedure in which an organ or tissue, such as bone tissue, is transplanted, or attached to a damaged, missing, or defective part of the body. This treatment concept in a patient is useful in eliciting a healing response from the recipient bone, thus improving recovery of the patient. There is also a relatively low risk of this autograft bone being rejected, this since the autograft bone originated from the patient's own body. This treatment concept however bears additional risks for the patient since an additional surgical site is required, in effect adding another potential location for post-operative pain and other complications. Further, this treatment concept of using autograft bone material in reconstruction of bone cavities or large bone defects is relatively expensive and time consuming.

Another treatment concept is to use allograft bone material taken from an individual other than the one receiving the bone graft. Doctors often use an allograft bone, typically from a dead, frozen bone, instead of an autograft bone in bone grafting because of the relatively high risk of complications with the additional surgical site required with autologous bone transplants. However, this treatment concept of using allograft bone material has the inherent risk of transmitting bacteria's, prions, viruses or other pathogenic factors during the bone grafting. This risk cannot be completely excluded and immune reactions against foreign material may occur when using allograft bone material in reconstruction of bone cavities or large bone defects.

Another treatment concept, when treating bone cavities or defects, is to use alloplast material where the bone graft is made of plastic, metal, or other material foreign to the human body. Currently, alloplast material has a very limited regeneration capacity during bone grafting and fails to regenerate large bone defects, especially in those which are classified as one or two wall bone defects, e.g. vertical crest augmentation.

There is thus a need for an improved bone substitute structure to use in reconstruction of bone cavities and large bone defects and a method of manufacturing this bone substitute structure removing the above mentioned disadvantages.

DESCRIPTION OF INVENTION

The present invention relates to the field of reconstruction of bone cavities and bone defects within reconstructive surgery.

The present invention refers to a manufacturing process of an individualized alloplast bone regeneration material functioning as a bone substitute for reconstruction of bone material in a patient. Pasteous alloplasts, i.e. alloplast having a pasty composition, the patient's blood and the patient's own growth factors are printed by a rapid prototype (prototyping) machine. The consecutively release of these components forms a three dimensional synthetic regeneration material, i.e. an individualized bone substitute structure, that is penetrated by blood fibrin and blood growth factors and thereby enable a complete replacement of the alloplast construct by the patient's own bone. This manufacturing process gets its information input via CAD/CAM (Computer-Aided Design and Computer-Aided Manufacturing) technology, it is computer controlled and runs under sterile and chairside conditions. A complete penetration with blood, the availability of growth factors, a reestablished vascularization and the invasion of bone forming cells are requirements for a successful alloplast replacement by patient own bone. Additional factors that are indispensable for an optimal regeneration process are accuracy of fit to the bone cavity or bone defect, stability of the whole construct, fixation of the material avoiding movements and the appropriate interconnecting porosity enabling an optimal osteoconductivity. By manufacturing a bone substitute structure in a rapid prototype machine and using the patient's own blood and growth factors according to the invention the above mentioned additional factors enabling optimal regeneration is obtained.

The present invention provides a bone substitute structure having a relatively high regeneration capacity, thereby focusing on the healing capacity of the patient since the patient's own blood and the growth factors have the potency to support the wound and bone defect regeneration.

It is desirable to provide a manufacturing process of an individualized alloplast bone regeneration material functioning as a bone substitute for reconstruction of bone material in a patient which provides a bone substitute structure with optimal biocompatibility, osteoconductivity, stability and defined geometry.

The object of the present invention is to suggest an improved and easy to implement method of manufacturing a bone substitute structure, wherein the method and the bone substitute structure improves the biocompatibility, osteoconductivity and stability for a reconstruction of bone cavities.

The present invention is defined by the appended independent claims. Various examples of the invention are set forth by the appended dependent claims as well as by the following description and the accompanying drawings.

With the above description in mind, then, an aspect of the present invention is to provide an improved solution of manufacturing a bone substitute structure and thereby enabling an optimized bone regeneration material to be used in reconstructive surgery which seeks to mitigate, alleviate, or eliminate one or more of the above-identified deficiencies in the art and disadvantages singly or in any combination.

The object is achieved by the features of claim 1 wherein, a method of manufacturing bone substitute structure for reconstruction of bone material in a patient, characterized in that the method comprises the steps of:

I. providing data reflecting a cavity in a bone of a patient;
II. defining and modelling a three dimensional structure corresponding to the cavity in the bone; and
III. providing an individualized bone substitute structure, corresponding to the defined and modeled three dimensional structure in step II, by combing calcium phosphate cement, growth factors and the patient's own un-coagulated blood.

Thus, the present invention manufactures an individualized and synthetic bone graft material using the patient's individual resources, i.e. the patient's own blood and growth factors stored in platelets, whereby wound and bone defect regeneration can be optimized. However, the growth factors taken from the platelets of the patient can be exchanged by bone morphogenetic proteins, such as for example rh BMP-2, rh BMP-4, rh BMP-7. No additional surgical site is required when providing and transplanting the bone substitute structure manufactured according to the invention. By manufacturing the bone substitute structure according to the invention the amount of biological material in the bone substitute structure can be controlled. By manufacturing the bone substitute structure according to the invention the bone substitute structure can be manufactured in any suitable geometry, suitable for the reconstruction of the bone material in the patient.

According to a further advantageous aspect of the invention, the data reflecting a cavity in a bone of a patient is obtained by scanning the hard and soft tissue of the bone cavity, and generating a digital data impression of the bone cavity.

According to a further advantageous aspect of the invention, that the three dimensional structure corresponding to the cavity in the bone is obtained by using a computer-aided design (CAD) software creating a virtual replacement based on the data reflecting the bone cavity.

According to a further advantageous aspect of the invention, the individualized bone substitute in step III is obtained by using a rapid prototype machine to generate the individualized bone substitute by additive layer manufacturing, wherein a layer upon layer sequence of the calcium phosphate cement, the individualized growth factors and the individualized un-coagulated blood prints the individualized bone substitute structure.

According to a further advantageous aspect of the invention, the rapid prototype machine which generates the individualized bone substitute comprises at least a first printing tube for the calcium phosphate, a second printing tube for the individualized un-coagulated blood and a third printing tube for the growth factors, wherein these at least three printing tubes are computer controlled regarding flow-rate and the layer upon layer sequence.

According to a further advantageous aspect of the invention, the calcium phosphate cement has a pasty composition during printing and then hardens when combined with the un-coagulated blood.

According to a further advantageous aspect of the invention, the growth factors are bone morphogenetic proteins, such as for example rh BMP-2, rh BMP-4, rh BMP-7, or the patient's own growth factors obtained from the platelets.

According to a further advantageous aspect of the invention, the method manufacturing bone substitute structure for reconstruction of bone material in a patient further comprises the step of hardening the individualized bone substitute structure. This hardening step involves hardening the three dimensional bone substitute structure in either additional blood from the patient or in a physiological solution. Thus, according to a further advantageous aspect of the invention, the hardening is obtained by positioning the individualized bone substitute structure in physiological solution, or by positioning the individualized bone substitute structure the patient's own un-coagulated blood.

The object is further achieved by an individualized bone substitute structure for reconstruction of bone material in a patient comprising calcium phosphate cement, growth factors, and the patient's own un-coagulated blood.

According to a further advantageous aspect of the invention, the calcium phosphate cement constitute more than 95% of the individualized bone substitute structure, preferably more than 97%.

By using the bone substitute structure according to the invention an optimal biocompatibility, osteoconductivity and stability can be achieved for a reconstructive surgery.

Any of the advantageous features of the present invention above may be combined in any suitable way.

A number of advantages are provided by means of the present invention, for example:

a chairside manufacturing process of the bone substitute structure, providing a bone substitute structure with optimal biocompatibility, geometry, stability and osteconductivity is obtained;
an improved, accurate and more robust manufacturing process of an individualized bone substitute structure is obtained;
a solution which enables a manufacturing of a unsymmetrical bone substitute structure to be is obtained;
a cost efficient and robust manufacturing process of a biocompatible bone substitute structure is obtained;
a bone substitute having an improved bio compatibility is obtained.

BRIEF DESCRIPTION OF THE DRAWINGS

The present invention will now be described in detail with reference to the figures, wherein:

FIG. 1 schematically shows a pictorial representation of a flow chart for the process of manufacturing a bone substitute structure according to the present invention.

It should be added that the following description of the examples is for illustration purposes only and should not be interpreted as limiting the invention exclusively to these examples/aspects.

DETAILED DESCRIPTION

FIG. 1 is schematically illustrated.

The present invention is a method of manufacturing an individualized three dimensional bone substitute structure by printing calcium phosphate cement, a patient's own blood and growth factors in a sterile chamber.

The following examples of the present invention relate, in general, to the field of reconstruction of bone cavities and bone defects within reconstructive surgery, in particularly, to a method of manufacturing bone substitute structure for reconstruction of bone material in a patient, whereby the generated bone substitute structure can support wound and bone defect regeneration.

Examples of the present invention will be described more fully hereinafter with reference to the accompanying drawings, in which examples of the invention are shown. This invention may, however, be embodied in many different forms and should not be construed as limited to the examples set forth herein. Rather, these examples are provided so that this disclosure will be thorough and complete, and will fully convey the scope of the invention to those skilled in the art. Like reference signs refer to like elements throughout.

FIG. 1 shows a flow chart the process of manufacturing a bone substitute structure according to the present invention. Hereinafter, referring to FIG. 1, the method of the present invention is explained in detail.

First, provide data reflecting a cavity in a bone of a patient by using CAD/CAM generated digital data reflecting the hard and soft tissue in a cavity or a bone defect situation. Then, define a three dimensional structure in CAD corresponding to the cavity in the bone of the patient and then manufacture the individualized bone substitute structure in a rapid prototype machine where the individualized bone substitute structure corresponds to the defined three dimensional structure. Finally, the bone substitute structure can proceed through an additional hardening reaction where a final hardened individualized bone substitute structure is obtained.

The bone substitute structure is an individualized bone regeneration material. The rapid prototype machine is positioned in a close box separating the inner sterile conditions from the unsterile environment. Sterility can be obtained in any suitable way such as for example by using suitable equipment such as UV-light.

The transport of disposables, such as printing tubes of the rapid prototype machine and Petri-dishes, in and out of the closed box and also removal of the finally printed bone substitute structure, i.e. bone regeneration material, occurs via an air lock in the rapid prototype machine. Sterile gloves are elements of the closed box and enable a manual work inside the closed box without affecting the sterile conditions.

The rapid prototype machine has a minimum of three printing tubes that are computer controlled regarding flow-rate and sequence of activation. One of the printing tubes prints the matrix of the bone substitute structure. The matrix of the bone substitute structure consist of calcium phosphate cement, wherein the composition of the calcium phosphate cement is pasty while it is printed and then hardens when it get wet by liquids, for instance water or in blood. Another printing tube prints the patient's own blood. This blood is taken from the patient's vein. While the blood is printed the coagulation is intermitted by the use of CPDA, heparin, EDTA or other chemical agents. The third printing tube prints either the patient's own growth factors obtained from platelets or bone morphogenetic proteins, such as for example rh BMP-2, rh BMP-4 or rh BMP-7. PRP (platelet rich plasma) or pure platelets growth factors can be obtained by suitable techniques, such as for example the two step centrifugation process or other known techniques.

Calcium phosphate cement, patient's own blood and patient's own growth factors are printed by the rapid prototype machine in a subsequent mode. The printed calcium phosphate cement is taken up in a suitable tool, such as for example a Petri dish. The Petri-dish may be filled with un-coagulated blood.

The extruded calcium phosphate cement strands have a diameter of lower 300 micro-meter and a suitable pasteous consistency, in that it is injectable. The hardening reaction of the calcium phosphate cement shell starts immediately when it gets wetted. During the hardening reaction of the calcium phosphate cement a micro-porosity is generated. The temperature of calcium phosphate in the hardening reaction shall not exceed 40 degrees.

The alternate printing of components (calcium phosphate, patient's own blood, the patient's own growth factors or BMPs) generates an individualized bone substitute structure, that has a stable three dimensional structure with adjustable porosity, where the individualized bone substitute structure is penetrated by the patient's own un-coagulated blood that in the presence of the pasty calcium phosphate cement coagulates, and where the individualized bone substitute structure is penetrated by a fibrin network.

The method of manufacturing the individualized bone substitute structure and the individualized bone substitute structure according to the invention may be used in any type of appropriate bone grafting treatment.

The invention is not limited to the example described above, but may be modified without departing from the scope of the claims below.

The terminology used herein is for the purpose of describing particular examples only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

The foregoing has described the principles, preferred examples and modes of operation of the present invention. However, the invention should be regarded as illustrative rather than restrictive, and not as being limited to the particular examples discussed above. The different features of the various examples of the invention can be combined in other combinations than those explicitly described. It should therefore be appreciated that variations may be made in those examples by those skilled in the art without departing from the scope of the present invention as defined by the following claims.

The invention claimed is:

1. A method of manufacturing a bone substitute structure in reconstruction of bone material in a patient, the method comprising:
   I. providing data reflecting a cavity in a bone of a patient;
   II. defining and modelling a three dimensional structure corresponding to the cavity in the bone; and
   III. providing an individualized bone substitute structure, corresponding to the defined and modeled three dimensional structure in II, by combining calcium phosphate cement, growth factors and the patient's own un-coagulated blood, wherein the individualized bone substitute structure in III is obtained by using a rapid prototype machine to generate the individualized bone substitute structure by additive layer manufacturing, wherein a layer upon layer sequence of the calcium phosphate cement, the individualized growth factors and the individualized un-coagulated blood prints the individualized bone substitute structure, and wherein the rapid prototype machine comprises at least a first printing tube for the calcium phosphate cement, a second printing tube for the individualized un-coagulated blood and a third printing tube for the growth factors, wherein these at least three printing tubes are computer controlled regarding flow-rate and the layer upon layer sequence, wherein the layer upon layer sequence comprises:
  first, printing a matrix of the individualized bone substitute structure comprising the calcium phosphate cement;
  subsequently, printing the individualized un-coagulated blood; and
  subsequently, printing the individualized growth factors.

2. The method according to claim 1, wherein the data in I is obtained by:
  scanning the hard and soft tissue of the bone cavity, and generating a digital data impression of the bone cavity.

3. The method according to claim 1, wherein the three dimensional structure in II is obtained by:
  using a computer-aided design (CAD) software creating a virtual replacement based on the data in I reflecting the bone cavity.

4. The method according to claim 1, wherein the un-coagulated blood hardens the calcium phosphate cement.

5. The method according to claim 1, wherein the growth factors are bone morphogenetic proteins or the patient's own growth factors obtained from the platelets.

6. The method according to claim 1, the method comprising:
  IV. hardening the individualized bone substitute structure from III.

7. The method according to claim 6, wherein the hardening in IV is obtained by:
  positioning the individualized bone substitute structure in a physiological solution, or
  positioning the individualized bone substitute structure in the patient's own un-coagulated blood.

8. An individualized bone substitute structure in reconstruction of bone material in a patient comprising calcium phosphate cement, growth factors, and the patient's own un-coagulated blood, wherein the individualized bone substitute structure is produced in a method according to claim 1.

9. The individualized bone substitute structure according to claim 8, wherein the calcium phosphate cement constitute more than 95% of the individualized bone substitute structure.

10. The individualized bone substitute structure according to claim 9, wherein the calcium phosphate cement constitute more than 97% of the individualized bone substitute structure.

* * * * *